United States Patent
Liang et al.

(10) Patent No.: US 7,919,521 B2
(45) Date of Patent: Apr. 5, 2011

(54) FIVE-MEMBERED IMINOCYCLITOL DERIVATIVES AS SELECTIVE AND POTENT GLYCOSIDASE INHIBITORS: NEW STRUCTURES FOR ANTIVIRALS AND OSTEOARTHRITIS THERAPEUTICS

(75) Inventors: Pi-Hui Liang, Hsinchu (TW); Yi-Ling Lin, Taipei County (TW); Chi-Huey Wong, Rancho Santa Fe, CA (US)

(73) Assignee: Academia Sinica, Mankang, Taipei (TW)

( * ) Notice: Subject to any disclaimer, the term of this patent is extended or adjusted under 35 U.S.C. 154(b) by 0 days.

(21) Appl. No.: 12/086,025

(22) PCT Filed: Dec. 5, 2006

(86) PCT No.: PCT/US2006/046348
§ 371 (c)(1),
(2), (4) Date: Aug. 14, 2008

(87) PCT Pub. No.: WO2007/067515
PCT Pub. Date: Jun. 14, 2007

(65) Prior Publication Data
US 2009/0306174 A1 Dec. 10, 2009

Related U.S. Application Data

(60) Provisional application No. 60/742,406, filed on Dec. 5, 2005.

(51) Int. Cl.
*C07D 207/00* (2006.01)
*A61K 31/40* (2006.01)
(52) U.S. Cl. .................................... 514/426; 548/556
(58) Field of Classification Search .................. 514/426; 548/556
See application file for complete search history.

(56) References Cited

OTHER PUBLICATIONS

Liang et al., Novel Five-Membered Iminocyclitol Derivatives as Selective and Potent Glycosidase Inhibitors: New Structures for Antivirals and Osteoarthritis, *ChemBioChem* 2006, 7, 165-173.
Liu et al., Synthesis and High-Throughput Screening of N-Acetyl-β-hexosaminidase Inhibitor Libraries Targeting Osteoarthritis, *J. Org. Chem.* 2004, 69, 6273-6283.
Block et al., Treatment of Chronic Hepadnavirus Infection in a Woodchuck Animal Model with an Inhibitor of Protein Folding and Trafficking, *Nature Medicine* vol. 4, No. 5 (1998).
Chen et al., Generation and Characterization of Organ-Tropism Mutants of Japanese Encephalitis Virus in Vivo and in Vitro, *Virology* 223, vol. 223, p. 79-88 (1996).
Chen et al., Persistence of Japanese Encephalitis Virus is Associated with Abnormal Expression of the Nonstructural Protein NS1 in Host Cells, *Virology* 217, 220-229 (1996).
Ellgaard et al., Quality Control in the Endoplasmic Reticulum, *Nature Reviews*, vol. 4, Mar. 2003.

Naoki Asano, Glycosidase Inhibitors: Update and Perspectives on Practical Use, *Glycobiology* vol. 13, No. 10, pp. 93R-104R, 2003.
Dwek, et al., Targeting Clycosylation as a Therapeutic Approach, *Nature Reviews*, vol. 1 (2002) p. 65-75.
GD Searle, Glycosylation Inhibitors in Biology and Medicine, *Structural Biology*, 1995, 5:605-611.
Lew et al., Discovery and Development of GS 4104 (oseltamivir): An orally Active Influenza Neuraminidase Inhibitor, *Current Medicinal Chemistry* (2000) 7, 663-672.
Goss et al., A Phase I Study of Swainsonine in Patients with Advanced Malignancies, *Cancer Research* 54, 1450-1457 (Mar. 1994).
Gruters et al., Interference with HIV-induced syncytium formation and viral infectivity by inhibitors of trimming glucosidase, *Nature* vol. 330 (1987).
Walker et al., Inhibition of Human Immunodeficiency Virus Syncytium Formation and Virus Replication by Castanospermine, *Proc. Natl. Acad. Sci.* USA, vol. 84, pp. 8120-8124 (1987).
Block et al., Secretion of human hepatitis B virus is inhibited by the imino sugar N-butyldeoxynojirimycin, *Proc. Natl. Acad. Sci.*, vol. 91, pp. 2235-2239 (1994).
Mehta et al., Inhibition of Hepatitis B Virus DNA Replication by Imino Sugars Without the Inhibition of the DNA Polymerase: Therapeutic Implications, *Hepatology*, vol. 33, No. 6, 2001.
Durantel et al., Study of the Mechanism of Antiviral Action of Iminosugar Derivatives against Bovine Viral Diarrhea Virus, *Journal of Virology*, vol. 75, No. 19 (2001).
Durantel et al., Effects of Interferon, Ribavirin, and Iminosugar Derivatives on Cells Persistently Infected with noncytopathic Bovine Viral Diarrhea Virus, *Antimicrobial Agents and Chemotherapy*, Feb. 2004, p. 497-504.
Courageot et al., α-Glucosidase Inhibitors Reduce Dengue Virus Production by Affecting the Initial Steps of Virion Morphogenesis in the Endoplasmic Reticulum, *Journal of Virology* (Jan. 2000) p. 564-572.
Wu et al., Antiviral Effects of an Iminosugar Derivative on Flavivirus Infections, *Journal of Virology*, vol. 76, No. 8 (Apr. 2002), p. 3596-3604.
Butters et al., Inhibition of Glycosphingolipid Biiosynthesis: Application to Lysosomal Storage Disorders, *Chem. Rev.* (2000), 100, 4683-4696.
Jian-Qiang Fan, A contradictory treatment for lysosomal storage disorders: inhibitors enhance mutant enzyme activity, Review: *Trends in Pharmacological Sciences* vol. 24, No. 7 Jul. 2003.
Welter et al., 2,5-Dihydroxymethyl 3,4-Dihydroxypyrrolidine Dans Les Feuilles De Derris Elliptica, *Phytochemistry*, vol. 15 pp. 747-749 (1976).
Card et al., 2(R),5(R)-Bis(hydroxymethyl)-3-(R),4(R)-dihydroxypyrrolidine. A Novel Glycosidase Inhibitor, *J. Org. Chem.* 1985, 50, 891-893.

(Continued)

*Primary Examiner* — San-ming Hui
*Assistant Examiner* — Kathrien Cruz
(74) *Attorney, Agent, or Firm* — Cohen Pontani Lieberman & Pavane LLP

(57) ABSTRACT

Novel 5-membered iminocyclitol derivatives were found to be a potent and selective inhibitors of the glycoprotein processing α- and β-glucosidase which were further found to be active antiviral agents against Japanese encephalitis virus, dengue virus serotype 2 (DEN-2), human SARS coronavirus and human β-hexosaminidase, a new target for development of osteoarthritis therapeutics.

5 Claims, 10 Drawing Sheets

OTHER PUBLICATIONS

Andersen et al., Two isosteric fluorinated derivatives of the powereful glucosidase inhibitors, 1-deoxynojirimycin and 2,5-dideoxy-2,5-imino-D-mannitol: Syntheses and glycosidase-inhibitory activities of 1,2,5-trideoxy-2-fluoro-1,5-imino-D-glucitol and of 1,2,5-trideoxy-1-fluoro-2,5-imino-D-mannitol, Carbohydrate Research 301(1997) 155-166.

Look et al., Enzyme-Catalyzed Organic Synthesis: Practical Routes to Aza Sugars and Their Analogs for Use as Glycoprocessing Inhibitors, Acc. Chem. Res. 1993, 26, 182-190.

Saotome et al., Combinatorial library of five-membered iminocyclitol and the inhibitory activities against glyco-enzymes, Chemistry & Biology 8 (2001) 1061-1070.

Takebayashi et al., A Versatile Synthetic Strategy for the Preparation and Discovery of New Iminocyclitols as Inhibitors of Glycosidases, J. Org. Chem. 1999, 64 5280-5291.

Wrodnigg et al., Probing the aglycon binding site of a β-glucosidase: a collection of C-1-modified 2,5-dideoxy-2,5-imino-D-mannitol derivatives and their structure-activity relationships as competitive inhibitors, Bioorganic & Medicinal Chemistry 12 (2004) 3485-3495.

Chang et al., Discovery of Picomolar Slow Tight-Binding Inhibitors of α-Fucosidase, Chemistry & Biology, vol. 11, (2004) p. 1301-1306.

Brik et al., A quick diversity-oriented amide-forming reaction to optimize P-subsit residues of HIV protease inhibitors, Chemistry & Biology, vol. 9, 891-896 (2002).

Shikhman et al., Profile of Glycosaminoglycan-degrading glycosidases and glycoside sulfatases secreted by human articular chondrocytes in homeostasis and inflammation, Arthritis & Rheumatism, vol. 43 No. 6, Jun. 2000, pp. 1307-1314.

Liu et al., Hexosaminidase Inhibitors as new drug candidates for the therapy of osteoarthritis, Chemistry & Biology 8 (2001) 701-711.

Perez-Alvarez et al., Structure-Hepatoprotective Activity Relationship of 3,4-Dihydroxycinnamic Acid (Caffeic Acid) Derivatives, J. Appl. Toxicol., vol. 21, pp. 527-531 (2001).

Natella et al., Benzoic and Cinnamic Acid Derivatives as Antioxidants: Structure-Activity Relation, J. Agric. Food Chem. (1999) vol. 47, pp. 1453-1459.

Tan et al., Chemical Modification of the Glucosidase Inhibitor 1-Deoxynojirimycin, Journal of Biological Chemistry, vol. 266, No. 22, Aug. 5, 1990, pp. 14504-14510.

Jacobs et al., [20] Metabolic Labeling of Glycoproteins with Chemical Tags through Unnatural Sialic Acid Biosynthesis, Methods in Enzymology, vol. 327 p. 260-275, 2000.

Mellor et al., Membrane disruption and cytotoxicity of hydrophobic N-alkylated imino sugars is independent of the inhibition of protein and lipid glycosylation, Biochem J. (2003) 374, pp. 307-314.

Mehta et al., Imino sugars that are less toxic but more potent as antivirals, in vitro, compared with N-n-nonyl DNJ, Antiviral Chemistry & Chemotherapy 13:5 (2002).

McGuigan et al., Potent and Selective Inhibition of Varicella-Zoster Virus (VZV) by Nucleoside Analogues with an Unusual Bicyclic Base, J. Med. Chem. 1999, 42 4479-4484.

Zitzmann et al., Imino sugars inhibit the formation and secretion of bovine viral diarrhea virus, a pestivirus model of hepatitis C virus: Implications for the development of broad spectrum anti-hepatitis virus agents, PNAS, vol. 96:No. 21, (1999).

Wu et al., Small molecules targeting severe acute respiratory syndrome human coronavirus, PNAS vol. 101, No. 27 (2004).

A. XTT

B. IFA

Scheme 1

α-glucosidase          β-glucosidase

Scheme 3

30

31 (m = 3)  35 (m = 7)
32 (m = 4)  36 (m = 8)
33 (m = 5)  37 (m = 9)
34 (m = 6)  38 (m = 11)

39 (m = 6)
40 (m = 7)
41 (m = 8)

Scheme 4

FIVE-MEMBERED IMINOCYCLITOL DERIVATIVES AS SELECTIVE AND POTENT GLYCOSIDASE INHIBITORS: NEW STRUCTURES FOR ANTIVIRALS AND OSTEOARTHRITIS THERAPEUTICS

PRIORITY CLAIM

This is a U.S. national stage of application No. PCT/US06/46348, filed on Dec. 5, 2006. Priority is claimed on the following application(s): Country: United States, Application No.: 60/742,406, Filed: Dec. 5, 2005 the content of which is incorporated here by reference.

BACKGROUND OF THE INVENTION

Field of the Invention

This present invention relates to new potent inhibitors of human N-acetyl β-hexosaminidase, which is the dominant glycosyaminoglycan-degrading glycosidase released by the chrondrocytes into the extracellular compartment, and is the dominant glycosidase in synovial fluid from patients with osteoarthritis.[29] Inhibitors of this enzyme could be used in the treatment of osteoarthritis.[30]

Glycosidases are involved in the biosynthesis and processing of the oligosaccharide chains of N-linked glycoproteins in the endoplasmic reticulum (ER) (FIG. 1).[1] Inhibition of these glycosidases has profound effect on the glycan structure and consequently affects the maturation, transport, secretion, and function of glycoproteins, and could therefore alter cell-cell or cell-virus recognition processes.[2-4] The neuraminidase inhibitor Tamiflu, for example, has been prescribed for the treatment of influenza virus infection.[5] The digestive α-glucosidase inhibitor, N-hydroxyethyldeoxynojirimycin (1, also called Glyset or Miglitol), has been used for the treatment of non-insulin-dependent diabetes.[6,7] Recent studies also showed that deoxynojirimycin (DNJ, 2, Scheme 1) and its derivatives (especially N-butyl DNJ) were potentially useful for treating several human diseases such as cancers,[8] viruses (AIDS,[9,10] hepatitis B,[11,12] hepatitis C,[13,14] and dengue[15,16]), and glycosphingolipid storage disorders.[17,18] The efficacy of iminocyclitols is attributed to their mimicry of the transition state of enzymatic glycosidic cleavage.[19]

The iminocyclitol 2,5-dideoxy-2,5-imino-D-mannitol (3, Scheme 1), a natural product,[20] is a powerful inhibitor of a large range of α- and β-glucosidase, even surpassing the activity of DNJ, which is frequently used as a standard.[19,21] The five membered iminocyclitols that carry hydroxyl groups of a specific orientation can mimic the shape and charge of the reacting sugar moiety of the transition state.[19,22,24] Since enzyme inhibition could be significantly enhanced with slight modifications at the aglycon moiety,[25-27] iminocyclitols could be used as common cores for development of selective glycosidase inhibitors through identification of an additional group to occupy the aglycon space. To quickly find such a group for attachment to the 5-membered iminocyclitol, we decided to conduct a combinatorial modification of compound 4 (Scheme 2) at the amine group in microtiter plates followed by screening in situ, a strategy successfully applied to other enzymes.[27,28] We initially screened the library for inhibitors of a panel of glycosidases in vitro, the potent α-glucosidase inhibitors identified in the screen were then tested in cell-based assays against Japanese encephalitis virus (JEV), dengue virus serotype 2 (DEN-2), as well as severe acute respiratory syndrome coronavirus (SARS-CoV).

BRIEF SUMMARY OF THE INVENTION

Based on the structure of 1-amino-1,2,5-dideoxy-2,5-imnio-D-mannitol (4), the invention applied a combinatorial synthesis in microtiter plates for in situ screening. This method is a powerful procedure to rapidly identify significant binding site differences among similar enzymes and develop potent and selective inhibitors. For the inhibitors of α-glucosidase, structures with bicyclic rings such as indole and naphthalene gave the best inhibitory potency, as illustrated by 24 with a $K_i$ value of 53 nM and 100-fold increase in activity compared to parent core 4. The N-alkylated derivatives of compound 24 were also tested for antiviral activity, and 36-38 with lipophilic alkyl groups were the most active with an $IC_{50}$ of about 5-10 μM to JEV, DEN-2 and SARS-CoV infection.

Given its important role in osteoarthritis, the inhibition of N-acetyl-β-hexosaminidase was investigated with regard to the substituent effects on the C1 nitrogen and ring nitrogen of core 4. The results showed that the acetamido group at the C1 position was crucial, with modification at the ring nitrogen with aromatic groups causing loss in inhibition. However, extending the alkyl chain at the ring nitrogen gave the most potent human β-hexosaminidase inhibitor known to date, that is, compound 54, with a $K_i$ value of 2.6 nM. Modeling indicated strong binding of compound 54 with β-hexosaminidase in its lipophilic cleft and an ionic interaction with the secondary binding site. Altogether, this work clearly demonstrates the effectiveness of our simple strategy of combinatorial approach for the rapid discovery of potent inhibitors as potential candidates for medical applications.

One embodiment of the present invention is a novel inhibitor of hexoaminidase or glucosidase represented by the following structure:

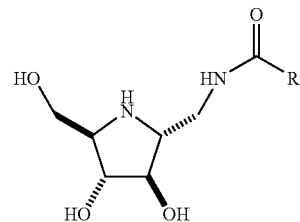

wherein R is selected from alkyl, cyclic and acyclic alkyl, aryl, cyclic and acyclic acyl, heteroalkyl, heterobicyclic, heteroaryl, acylaryl, acylheteroaryl, alkylaryl, alkylheteroaryl, sulfanylalkyl, alkylsulfanylaryl and acceptable salts thereof.

Preferably, R is an un-substituted or substituted indole or

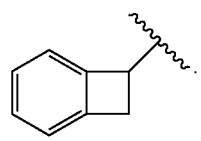

Another embodiment of the present invention is a novel inhibitor of hexoaminidase or glucosidase represented by the following structure:

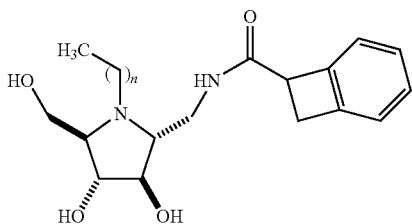

wherein n is an integer ranging from 3-11. These novel inhibitors may be used in treating infection of Japanese encephalitis virus or dengue virus serotype 2 by administering to a patient in need thereof an effective amount of the inhibitors.

Another embodiment of the present invention is a novel inhibitor of hexoaminidase or glucosidase represented by the following structure:

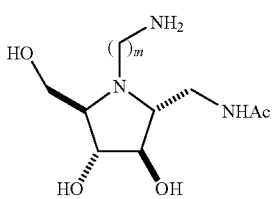

wherein m is an integer ranging from 6-8, preferably 7.

Another embodiment of the present invention is a novel inhibitor of hexoaminidase or glucosidase represented by the following structure:

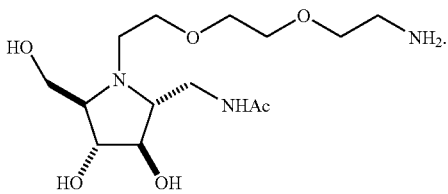

The present invention provides a method of treating a subject having arthritis by administering an inhibitor, such as those discussed above, to the subject of sufficient quantity for inhibiting hexoaminidase or glucosidase activity within the subject.

DETAILED DESCRIPTION OF THE INVENTION

Figure 1:
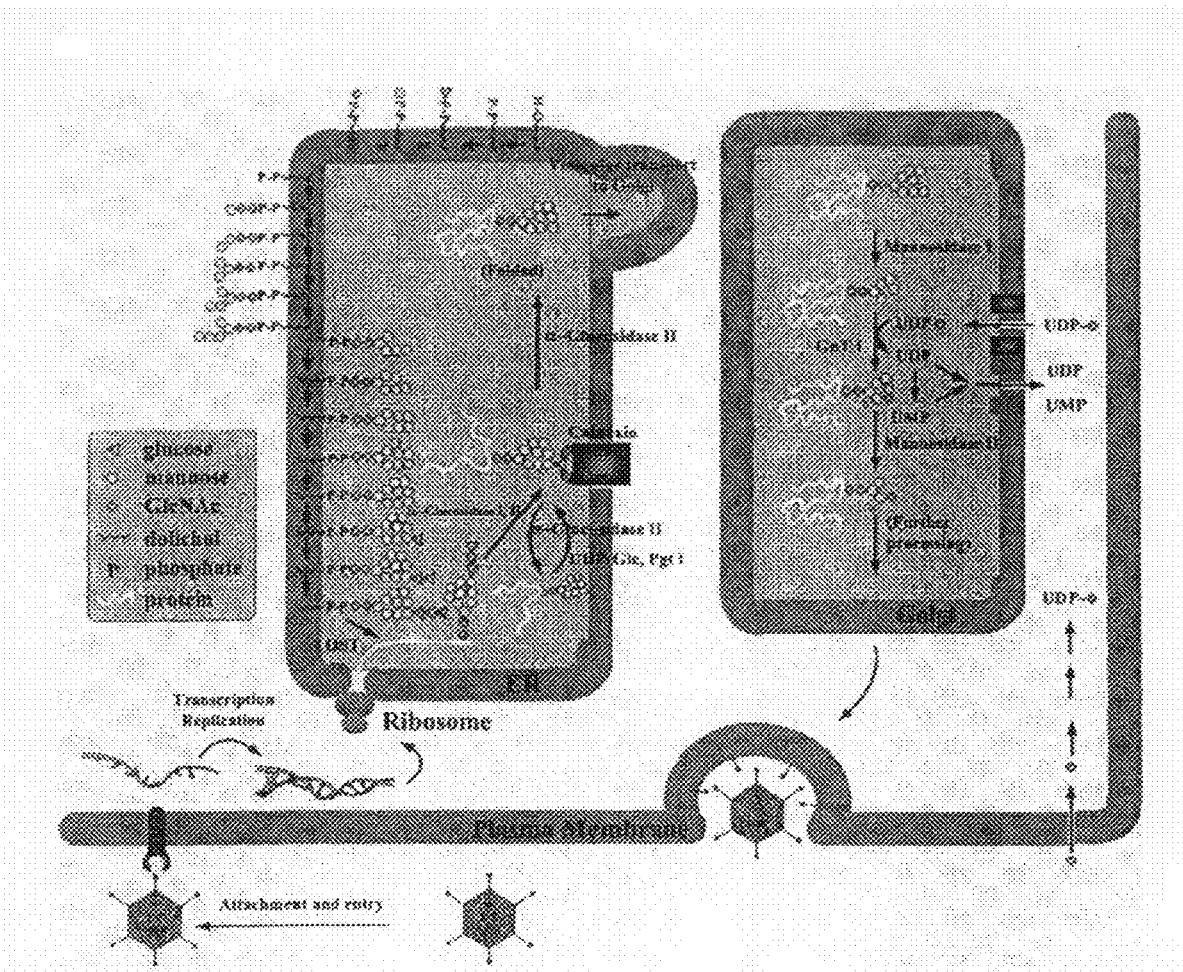
FIG. 1 illustrates the assembly of viral envelop glycoproteins involves the use of host enzymes such as glycosidases and glycosyltransferases. Inhibition of glycosidases could disrupt the process and inhibit viral replication.

Rapid combinatorial synthesis and high-throughput screening. The preliminary inhibitory assays of core 4 showed a broad inhibitory spectrum for glycosidases, except for α-, β-galactosidase and β-mannosidase (see supporting information). Because core 4 had only moderate inhibitory activities against α-mannosidase and α-fucosidase, the library generated from 4 was screened against α-, β-glucosidase and N-acetyl-β-hexosaminidase in this study.

A mixture of iminocyclitol 4, a carboxylic acid (1 equiv, Scheme 2), diisopropyl ethylamine (DIEA, 2.2 equiv), and (1H-benzotriazole-1-yl)-1,1,3,3-tetramethyl-uronium hexafluorophosphate (HBTU, 1.1 equiv) in DMSO was shaken in 96-well microtiter plates for 5 h. Crude reaction products were randomly selected (30%) and analyzed by ESI-MS to ensure the presence of the desired products. The reaction mixture was diluted by appropriate buffer solutions and transferred to another 96-well microtiter plate for screening directly without any purification. Based on the $IC_{50}$ values of 4 (see supporting information), the concentrations of reaction products were set at 20 μM for α-, β-glucosidase and 30 μM for β-hexosaminidase. Assuming the amide formation is complete, the percentage of inhibition relative to the control was calculated on the basis of absorbance at 405 nm for p-nitrophenol released from their corresponding substrates.

Of the 144 compounds generated from the amide-forming reaction, several inhibitors were found (see Supporting information). Good inhibitors for each enzyme were selected, re-synthesized as pure compounds, and reevaluated for determination of $IC_{50}$ or $K_i$ values (Table 1, Scheme 2). In the screen of α-glucosidase (baker's yeast) inhibition, about two-thirds of reaction products were found to be more potent than 4 (see Supporting information for overall library inhibitory activities). Briefly, α-glucosidase was inhibited to a greater extent when the compound contained a fused-aromatic ring (e.g. 17 and 25) and a heteroaromatic component (e.g. 19-21) although this doesn't account for 7. It is worth noting that the enzyme was more interactive with a bi-cyclic than a tri-cyclic, or a mono-cyclic aglycon (e.g. 16 vs. 25 vs. 10). The α-glucosidase from Bacillus stearotherinophilus was also investigated with the same library. The results were similar to that for baker's yeast. The most potent one against yeast α-glucosidase was compound 24 with a $K_i$ value of 53 nM and 600-fold selectivity for α- over β-glucosidase. Interestingly, the $IC_{50}$ values of compounds 15-17 for α-glucosidase were about two to three orders of magnitude difference. These results suggest that, while a lipophilic binding pocket exists that allow a bicyclic ring such as indole or naphthalene to fit, the specific orientation of these bi-cyclic rings is also very important.

In the screen of β-glucosidase (almonds), about one-sixth of the reaction products were found to be comparable or more potent than 4. C-1-modified α-iminocyclitols showed weaker effects for β-glucosidase than for α-glucosidase. A dimethylamino group attached to the aromatic ring could enhance the inhibitory activity (e.g. 11 and 29), as documented previously.[26] In particular, structures with a trans-cinnamic moiety were shown to significantly inhibit this enzyme, especially those with meta-halogen substituents (e.g. 12, 13 and 26). Because the trans-cinnamic moiety has a board range of biological properties including hepatoprotective,[31] anti-malarial,[32] and antioxidant,[33] our finding suggests a new application of trans-cinnamic acid and its derivatives. The most inhibitory was the reaction product 28 (up to 67% inhibition), with a $K_i$ value of 1.24 μM. In general, derivatives of 4 are more selective toward α-glucosidase than β-glucosidase as inhibitors.

Inhibition of N-acetyl-β-hexosaminidase seems to be greater when there are hydrophilic substituents in the C-1 position (e.g. 6, 8, and 9). However, none of the substituents is more potent than the acetamido group; this indicates its crucial role in the enzyme active site. This study also showed that potent inhibitors of β-hexosaminidase can be found from derivatives of 4, though relatively weaker inhibitors of β-glucosidase were observed.

Overall, the combinatorial synthesis followed by rapid screening in situ as described here provided a platform to identify selective glycosidase inhibitors through modification of a common transition-state core at the aglycon side chain.

Antiviral activities of 5-membered iminocyclitols. Endoplasmic reticulum (ER) α-glucosidase inhibitors, which block the trimming step of N-linked glycosylation, have been shown to eliminate the production of several ER-budding viruses.[34] Previously, we reported the anti-virus effects of a N-n-nonyl DNJ (NN-DNJ) on flavivirus infections.[16] However, five-membered iminocyclitols had not been tested for their antiviral activities. With the potent α-glucosidase inhibitors in hand, we tested their potential antiviral effect based on our previous assay system for JEV and DEN-2. Details of the anti-virus assay are given in the Experimental Section.

Compounds 7, 17, 20, 22, and 24 exhibited no inhibition at 50 and 100 μM (data not shown). The peracetylated compound 30, which is believed to increase the cellular uptake and is then converted to compound 24 by cellular esterases,[35] was subjected to the cell assay. However, it also showed no inhibition at 50 μM (data not shown). We then turned our attention to modify the ring nitrogen on the most potent α-glucosidase inhibitor 24. Side chain modification by alkylation of DNJ has been previously reported to enhance both the ability to inhibit glycan processing and virus production.[13,36-38]

Figure 2:
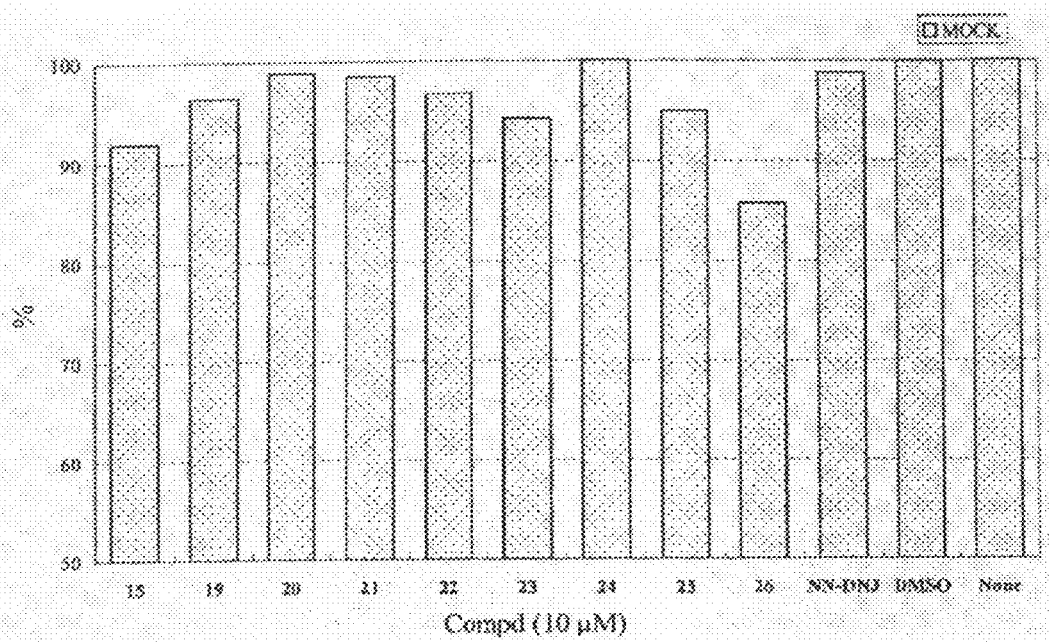
FIG. 2 Shows cell based assays of anti-JEV and anti-DEN effects of compounds 24, 31-38 and NN-DNJ (10 μM) (A) Cell survival was measured by XTT assays. Data are shown as the percentage versus the mock-infected BHK-21 cells without inhibitor treatment (none, 100%). (B) The viral protein expressions by IFA were read by Fluorescence Microplate Reader (Molecular Device) with excitation wavelength of 355 nm and the emission wavelength of 488 nm. Data are shown as the percentage versus untreated inhibitor one. (C) The culture supernatants were collected for viral titration by plaque forming assay. The virus titers are shown as PFU (plaque forming unit) per milliliter. Representative results from two independent experiments are shown here.
Figure 2:
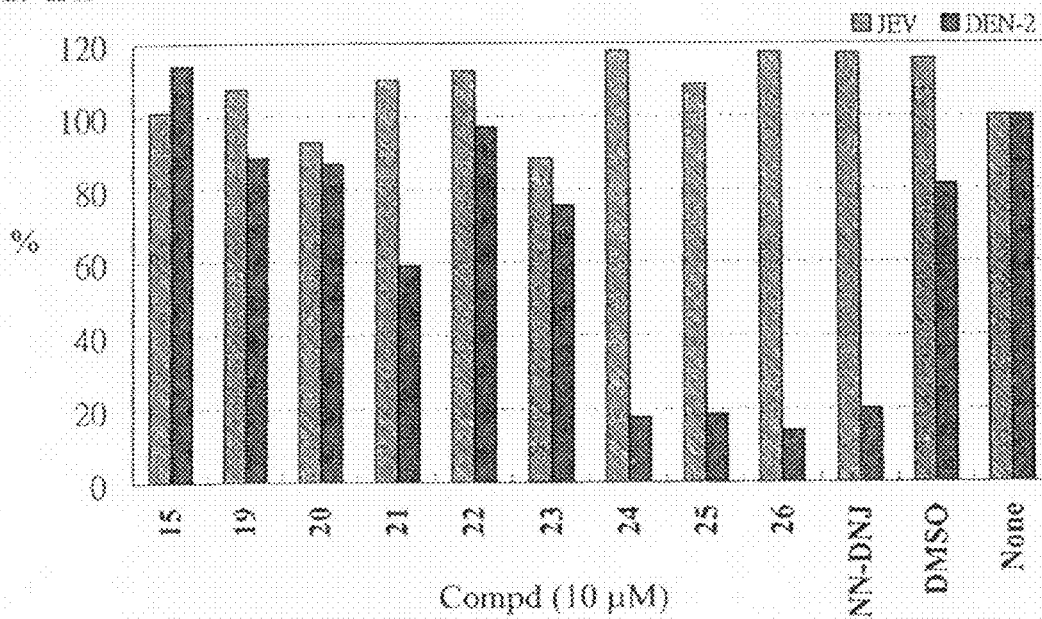
Figure 2:
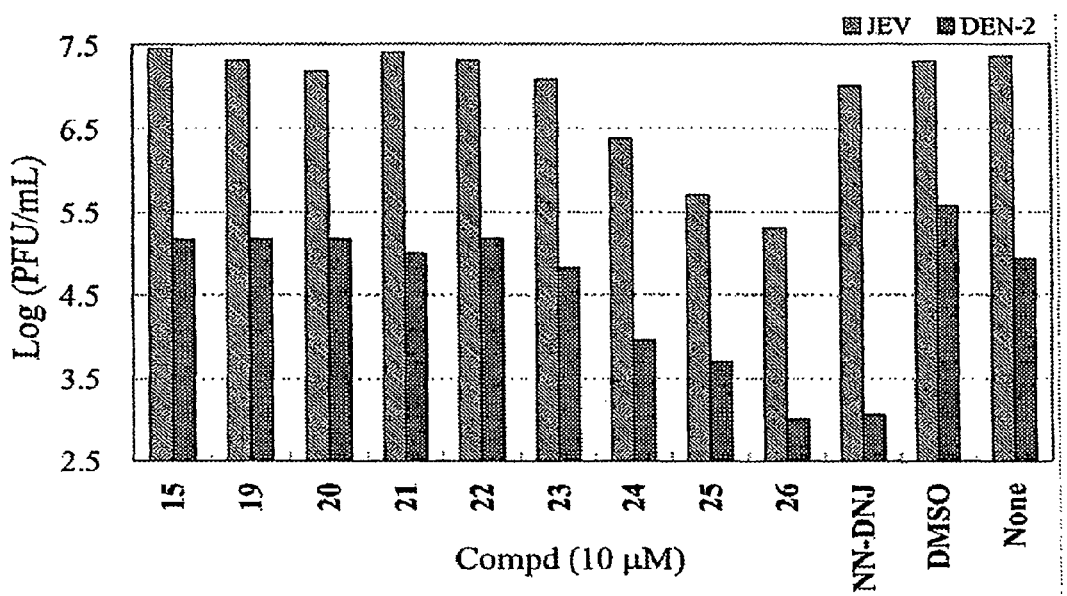
Figure 3:
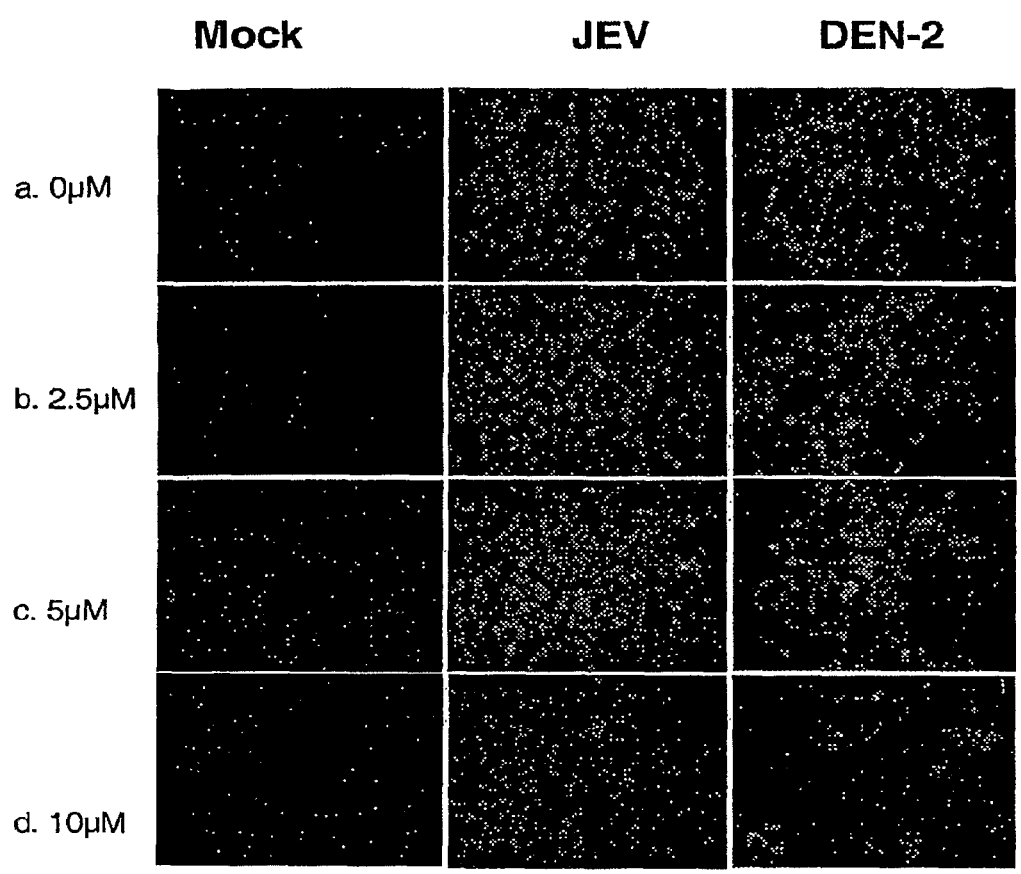
FIG. 3. Shows morphology of favivirus-infected BHK-21 cells. Cells infected with mock, JEV (MOI of 0.1) and DEN-2 (MOI of 0.1) were treated with various dose of inhibitor 37 as indicated. Two days postinfection, cells were fixed and stained with anti-JEV and anti-DEN NS3 MAb and a FITC-conjugated secondary antibody (green). Cell nuclei were stained by DAPI (blue). Pictures were taken using an inverted fluorescent microscope (Leica) with filters for FITC and DAPI and superimposed the pictures in the same fields.

To study the influence of the alkyl chain length on the cell based assay, a series of compounds with alkyl chain ranging from $C_4$ to $C_{12}$, attached to compound 24 was synthesized by using reductive amination with appropriate)aldehydes to give rise to compounds 31-38 (Scheme 3). Inhibition activities of N-alkylated derivatives against α-glucosidase, β-glucosidase were also investigated (see Supporting Information). The results showed that these molecules still have α-glucosidase selectivity, albeit in low activity compared to parent compound 24. This result was also observed in in vitro anti-α-glucosidase activity of DNJ and NN-DNJ. The cell based XTT assay, which measured cell proliferation, indicated that most of the compounds were not toxic at 10 μM (FIG. 2A). The exception compound 38, which showed a low level of cytotoxicity. In general, the alkylated iminocylitols were more active against DEN-2 than JEV infection (FIG. 2B). Relative to the virus titer derived from cells treated with NN-DNJ, these newly synthesized molecules were less potent to DEN-2 infection (FIG. 2C). However, in anti-JEV infection, compounds 36-38 were more potent than NN-DNJ. Compound 37 (FIG. 3) appeared to be a less cytotoxic and more potent one with $IC_{50}$=4.7 μM and $IC_{90}$=9.2 μM for DEN-2 (Table 2). In the present studies, compounds 36-38 with chain lengths of nine, ten, and twelve carbons, respectively, were found to be optimal for the antiviral activity. A similar effect was also noticed against varicella zoster virus.[39] Longer alkyl chains, such as, the decyl chain in compound 38, provided a modest increase in potency in cell-based assays, but also resulted in an increase in cytotoxicity, presumably due to the disruption of the lipid bilayer.[36]

From a structural perspective, the alkylated iminocyclitol can be viewed as consisting of two distinct molecular elements: (1) an imino sugar head group and (2) an N-alkyl side chain. The head group is recognized by the ER-α-glucosidase. The role of the tail, as shown in NN-DNJ, is unclear but it may be able to insert into the membrane to increase its local concentration near the membrane-associated ER glucosidase.[40] In recent studies, N-nonyldeoxygalactonojirimycin (NN-DGJ), a galactose-type iminocyclitol, was found to still has anti-HBV[12] and anti-BVDVI[13] activities, although it lacks the ability to inhibit α-glucosidase. These observations suggest that NN-DNJ might possess a different antiviral mechanism. Nevertheless, we found that NN-DGJ did not inhibit either JEV or DEN-2 in our cell-based assay system.[16] The weaker α-glucosidase inhibitors 39-41, derived from core 4 with eight to ten carbons (Scheme 3), were then evaluated and we found that 39-41 at 10 μm or 50 μM did not inhibit either JEV or DEN-2 infection (data not shown) in the cell-based assay.

Inhibitors 36-38 were also screened against the infection of SARS-CoV, following our previously established procedure.[41] The $IC_{50}$ for compound 37 was around 3.3~10 μM. The antiviral effects of compounds 36-38 on JEV, DEN-2, and SARS-CoV shown in the present study are likely mediated by its inhibition of the ER α-glucosidase; however the possibility of other mechanism besides α-glucosidase inhibition cannot be rigorously excluded.[16]

Discovery of potent human β-hexosaminidase inhibitors. In our previous study, compound 5 and its N-methyl derivative 42 ((2R,3R,4R,5R)-N-methyl-2-(acetamido-methyl)-3, 4-dihydroxy-5-(hydroxymethyl)pyrrolidine) were found to be potent inhibitors of human N-acetyl-β-hexosaminidases, with $K_i$=24 nM.[30] In particular, incubation of human chondrosarcoma cells with iminocyclitol 42 resulted in an accumulation of glycosaminoglycans (GAGs) in the cell-associated fraction and a decrease in the release of GAGs into the culture supernatant. The discovery of iminocyclitols as potential chondroprotective agents suggests a new avenue for the development of drugs to treat osteoarthritis.

In order to further improve the potency of 42, considerable effort has been directed toward modification of the ring nitrogen and the C1 nitrogen of iminocyclitol 4.[42] However, none of the synthesized inhibitors was more potent than compound 42. The structure-activity relationship of iminocyclitols revealed that the acetamido group at C1 position is crucial, and the active site pocket of β-hexosaminidase does not tolerate larger substituents. The methyl group at the ring nitrogen enhances the inhibition activity, whereas aromatic ring substituents cause a decrease in inhibition activity. Our alternative approach to increase potency is to probe a distant aglycon-binding site of β-hexosaminidase. We therefore decided to attach to attach a long-chain alkyl group with a terminal amine to the ring nitrogen through reductive amination. The resulting primary amine is easy to diversify with amide-bond formation to generate libraries as mentioned above.

Figure 4:
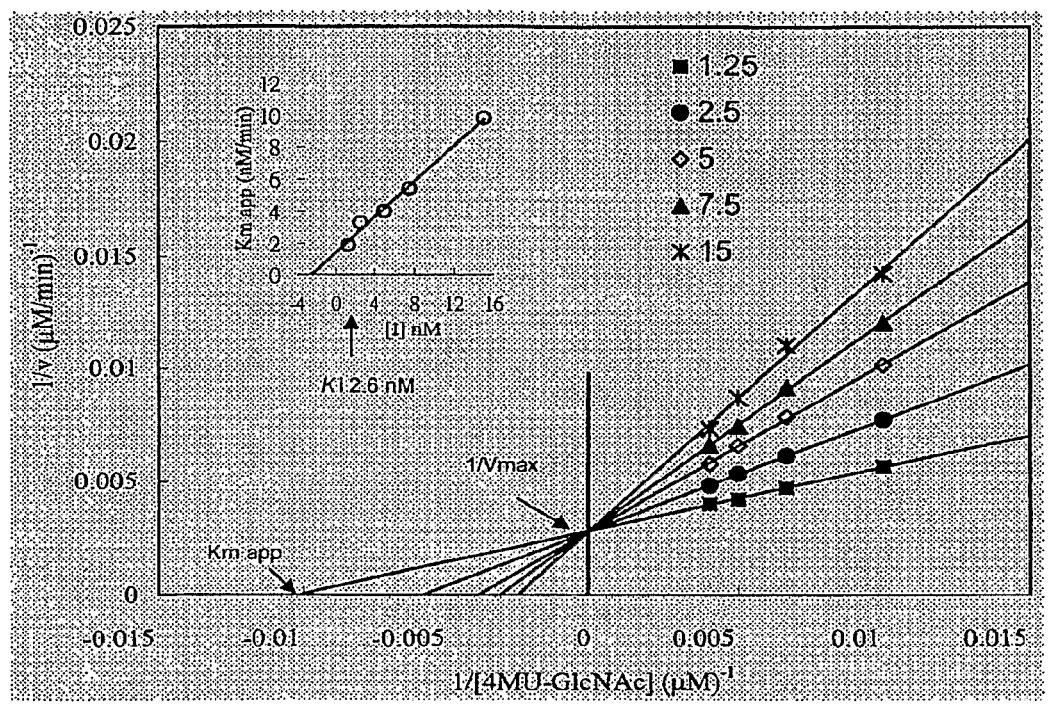
FIG. 4 shows Lineweaver-Burk double reciprocal plots of compound 54 were carried out to obtained $K_m$ app and $V_{max}$ values. Also $K_i$ value was obtained from a re-plot of the $K_m$ app and inhibitor concentrations. The $K_i$ value of each molecule is shown on the y axis.
Figure 5:
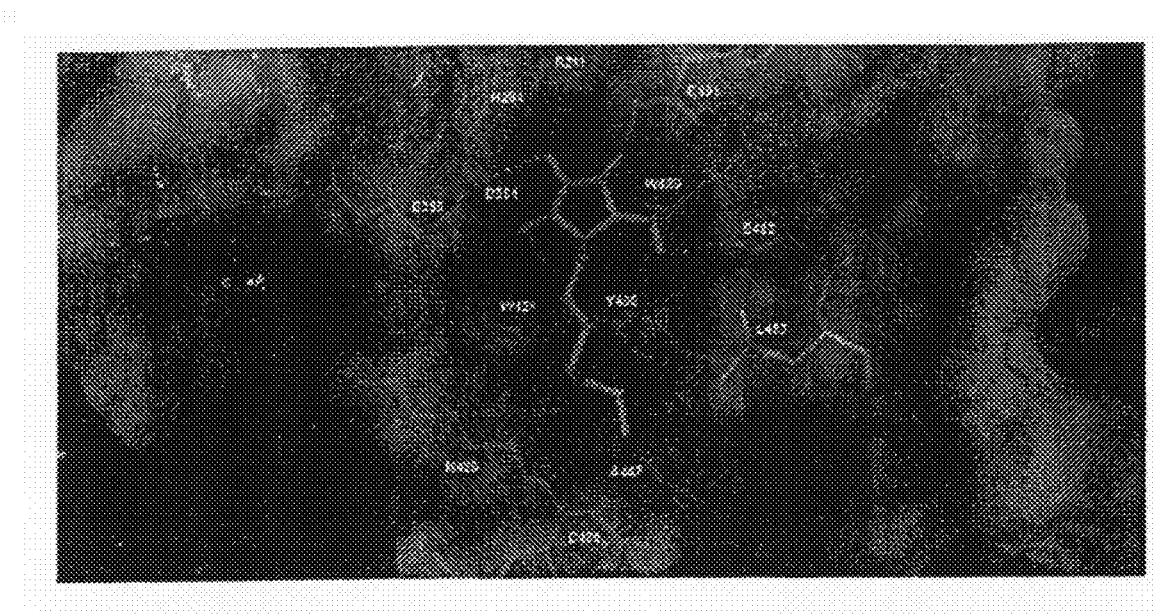
FIG. 5 shows a modeling complex of human β-hexosaminidase with the 54 (light gray at central). The hydroxy groups of the inhibitor could form hydrogen-bond interactions with residues R211, D355, D452, and E491. The C1 N-acetyl group of 54 is in hydrogen-bond interactions with D354 and its carbonyl group is in HB interactions with side-chain hydroxyl group of Y450. Computed molecular surface exhibits a narrow hydrophobic cleft near the binding site of the iminocyclitol ring. Additional binding affinity from the long alkyl chain could result from hydrogen-bond interactions of the end amino group with the backbone carbonyl of K425 and A447 or possible induced ionic interactions with the carboxyl group of D426. Figure produced with MGL-TOOLS.
Figure 6:
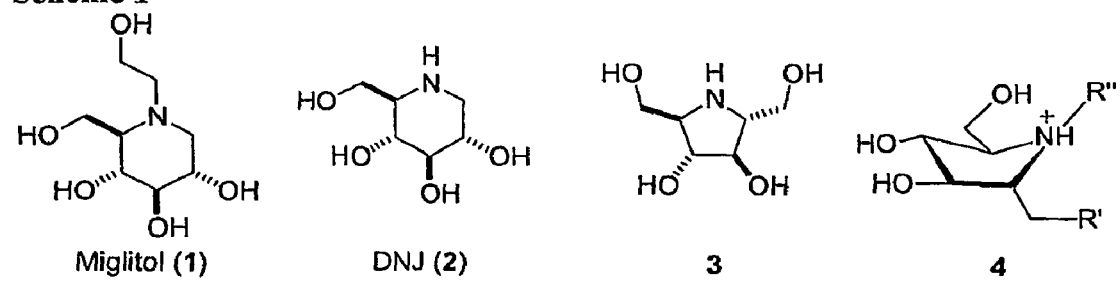
FIG. 6, Scheme 1 shows structures of iminocylitols 1 to 3 and representative transition states of α- and β-glucosidase catalyzed reactions showing the aglycon R. The five-membered iminocyclitol shown below is used for deivatization at R' and R" to probe the aglycon binding sites.
Figure 6:
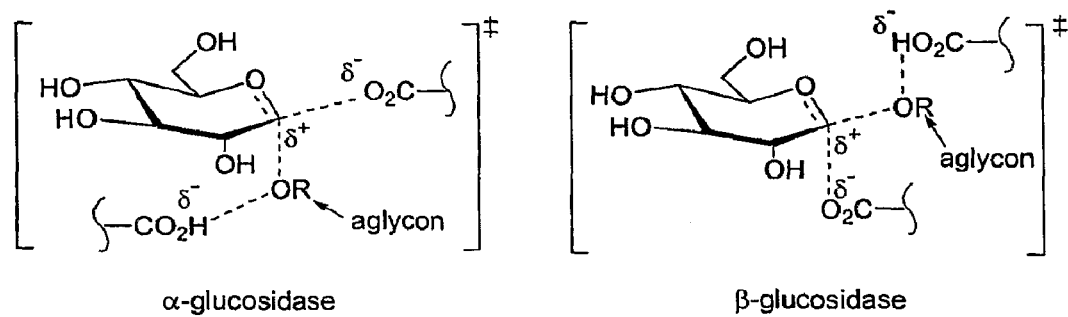
Figure 7:
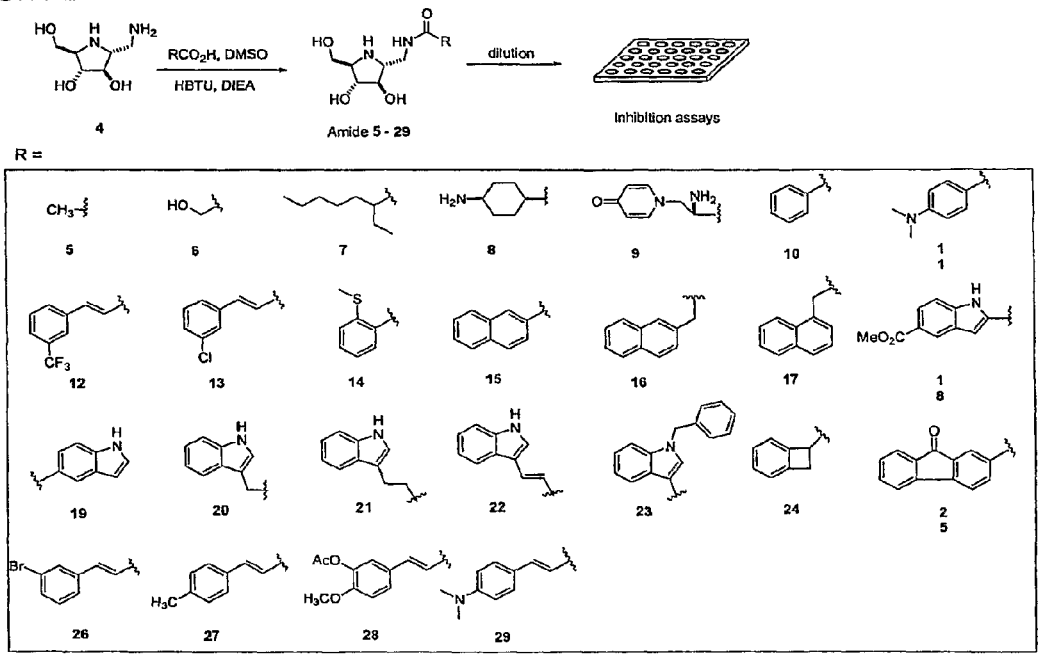
FIG. 7, Scheme 2 depicts the reaction of iminocylitol 4 with a library of carboxylic acids for the subsequent high-throughput screening in situ of glycosidase.
Figure 8:
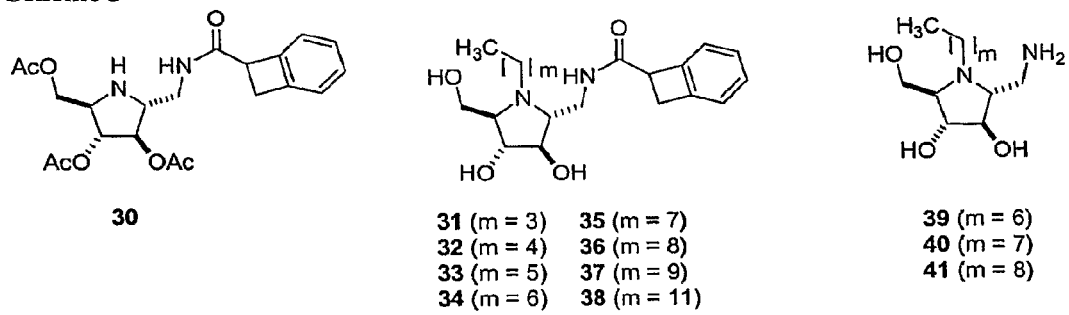
FIG. 8, Scheme 3 shows compounds 31-38 for anti-virus assays.
Figure 9:
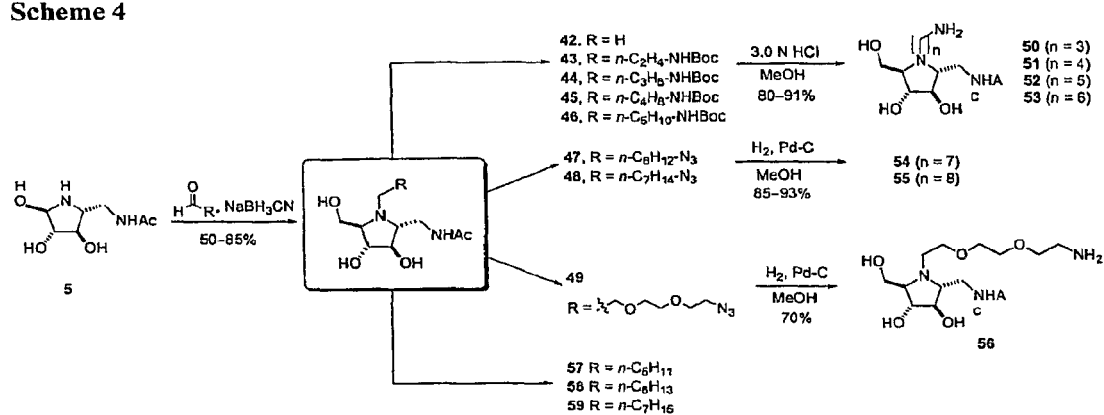
FIG. 9, Scheme 4 is the synthesis of hexosaminidase inhibitors 50-58.

Our strategy began with reductive amination of compound 5 with aldehydes of different lengths to give compounds 43-49 (FIG. 4). The intermediates were either deprotected under acidic conditions or hydrogenolysed to give primary amines 50-56. In our first attempt to generate a library from compound 50 by amide-bond formation as mentioned above, the high-throughput screening showed no compounds with significantly enhanced inhibitory activities (data not shown). Thus, the inhibition studies of compounds 51-56 against human placenta N-acetyl-β-hexosaminidase were carried out. 4-Methylumbelliferyl N-acetyl-β-D-glucosaminide (4-MN-GNAc) was used as the substrate. The apparent $K_m$ and $V_{max}$ values for each substrate were calculated from the Lineweaver-Burke double reciprocal plot of [1/v]/[1/S]. The $K_i$ values were determined from a replot of the $K_m$ (app) vs the inhibitor concentration. Compound 54 is the most potent competitive inhibitor with a $K_i$ value 2.6 nM (FIG. 4). Interestingly, in varying the linkage from N-propyl to N-octyl of compounds 51-55, we observed a trend in human β-hexosaminidase inhibition. Compound 54 with a heptamine moiety was the strongest inhibitor. In an attempt to further optimize the inhibitor, the linker was replaced by an ethylene glycol chain (hydrophilic linker) to give compound 56 ($K_i$=60 nM) and by moderate N-alkyl chains such as compounds 57, 58, and 59 ($K_i$=180 nM, 250 nm, and 160 nM, respectively). However, these modifications had a negative effect; this indicated the important role of the amino group and the lipophilic chain in compound 54. As the crystal structure of human β-hexosaminidase B is now avalible,[43] its complex with 54 was modeled to reveal a narrow hydrophobic cleft in the active site, which is mainly enclosed by the side-chain groups of residues W424, Y450, A1447, L453 and the backbone of residues K425 and D426 (FIG. 5). The amino group at the terminal site is expected to be largely protonated when binding with the enzyme. It presumably forms a salt bridge with the secondary aglycon binding site of the enzyme.[44] It appears that the alkyl linkage is long enough to bring the amine end near enough to have hydrogen-bond interactions with the backbone carbonyl of K425 and A447 and a possible ionic interaction with the carboxyl group of D426.

Experimental Section

Materials. The source of enzymes are as follows: α-glucosidase (EC 3.2.1.20) from baker's yeast and *Bacillus stearothermophilus*; β-glucosidase (EC 3.2.1.21) from almonds; α-galactosidase (EC 3.2.1.22) from *Aspergillus niger*; α-mannosidase (EC 3.2.1.24) from jack bean; β-mannosidase (EC 3.2.1.25) from snail acetone powder; N-acetyl-β-hexosaminidase (EC 3.2.1.52) from jack beans and human placenta. All of above enzymes were purchased from Sigma Co. (St. Louis, Mo.). β-Glucosidase from sweet almonds and β-galactosidase (EC 3.2.1.23) from *Escherichia coli* were purchased from Toyobo Co., Ltd. (Osaka, Japan). α-Fucosidase (EC 3.2.1.51) from human, a recombinant protein was a gift from Professor Chun-Hung Lin at Academia Sinica (Taipei, Taiwan).

General method for chemical synthesis. All non-aqueous reactions were run in oven-dried and vacuum-cooled glassware under an inert nitrogen atmosphere. Reactions were monitored by thin-layer chromatography (TLC, Merck, silica gel 60F-254) utilizing ninhydrin, p-anisaldehyde, or cerium molydate as the stain reagent. Silica gel used for flash column chromatography was Mallinckrodt type 60 (230-400 mesh). Unless otherwise noted, reagents and materials were obtained from commercial sources and used as provided without further purification. $^1$H and $^{13}$C NMR spectra were recorded on a Bruker AV-400 or AV-500 spectrometer and referenced to residual solvent peaks (CDCl$_3$: $^1$H δ 7.24, $^{13}$C δ 77.0; MeOH-d$_4$: $^1$H δ 3.30, $^{13}$C δ 49).

General procedure for coupling reactions and in situ screening. To a DMSO solution (10 μL) in each well of a 96-well microtiter plate was added each carboxylic acid (10 μL from a 10 mM stock solution in DMSO, 0.1 μmol), HBTU (10 μL from a 11 mM stock solution in DMSO, 1.1 equiv, 0.11 μmol), and DIEA (10 μL from a 22 mM stock solution in DMSO, 2.2 equiv, 0.22 μmol). The reaction was initiated by adding compound 4 (10 μL from a 10 mM stock solution, 0.1 μmol) to each well. The reaction mixtures were shaken at room temperature for 5 h and were monitored for completion based on the disappearance of 4 by TLC with mobile phase of CHCl$_3$/MeOH/NH$_4$OH (1/3/1, R$_f$=0.33). Then an aliquot (5 μL) was withdrawn from the previous reaction mixture and mixed with 95 μL phosphate buffer (pH 7.0) to reach a 20-fold dilution. The same procedure was repeated to give the desired dilution (i.e. a final concentration of 20 μM product in each well of a microtiter plate). In each well of another plate, α-glucosidase from baker's yeast (10 μL, 0.1 U/mL) and p-nitrophenyl-α-glucopyranoside (50 μL, 2 mM) were mixed with an aliquot (50 μL) of the aforementioned mixture and 90 μL buffer (to give ~20 μM inhibitor) for the enzyme inhibition assay.

Enzyme assay. General procedure for the assay with various glycosidases. The initial velocities of the hydrolysis were measured spectrophotometrically at various concentrations of p-nitrophenyl-glycopyranoside (4 mM, 2 mM, 1 mM, 0.5 mM, 0.25 mM, 0.125 mM, 0.0625 mm) at 405 nm using Bio Assay Reader (Perkin Elmer HTS 7000 Plus) at 30° C. The obtained data were fitted into the Michaelis-Menten equation by using the Kaleida Graph program to determine the apparent $K_m$ values. The substrate concentrations were used at 3-fold to 5-fold $K_m$ values for evaluation of the inhibitory effect against various glycosidases. To give an ideal progress curve, an appropriate enzyme concentration (0.01-0.2 Unit/mL) and inhibitor concentration (from 1 nM to 500 μM) were used. The 50% inhibitory concentration (IC$_{50}$) was determined as the concentration at which the velocity of the hydrolysis was reduced to 50% as compared to the untreated one. The assays performed in wells of the microtiter plate contained either sodium phosphate buffer (50 mM, pH 7, for α- and β-glucosidase, α- and β-galactosidase, α- and β-mannosidase, α-fucosidase), or McIlvaine's buffer (25 mM, pH 6, N-acetyl-β-hexosaminidase, jack bean).

The $K_i$ values of the inhibitors were determined by the double reciprocal plot (1/v vs. 1/[S]) to give apparent $K_m$ (the $K_m$ in the presence of inhibitors). The secondary plot was generated by plotting the apparent $K_m$ values as a function of inhibitor concentrations. $K_i$ was calculated from the negative value of the x-intercept of this plot.

Kinetic analysis of human placenta β-hexosaminidase. Incubations were performed in a total volume of 200 μL. Unless otherwise stated, reaction mixtures contained 100 mM citrate buffer (pH 4.5), various amount of 4-methylumbelliferyl N-acetyl-β-D-glucosaminide, and various amounts of inhibitors with 0.02 mU/well of β-hexosaminidase. After incubation for 15 min at 30° C., the reaction was terminated by the addition of 0.5 M sodium glycine buffer, pH 10.5. Enzyme activity was measured by the release of 4-methylumbelliferone with the excitation wavelength of 360 nm and the emission wavelength of 460 nm.

Cell lines, viruses, and virus infection. BHK-21 cells were cultured in RPMI 1640 medium containing 5% fetal bovine serum (FBS) and 2 mM L-glutamine. JEV strain RP-9 [45] and the Taiwanese DEN-2 strain PL046 [46] were used in this study. Virus propagation was carried out in C6/36 cells by using RPMI 1640 medium containing 5% FBS. Inhibitors were dissolved in DMSO. For infection with JEV or DEN-2, monolayers of BHK-21 cells in 6- or 12-well plates were adsorbed with virus for 1 h at 37° C. After adsorption, unbound viruses were removed by gentle washing with serum free medium, followed by addition of fresh medium containing various amounts of inhibitors for further incubation at 37° C. To determine virus titers, culture media were harvested for plaque-forming assays. Various virus dilutions were added to 80% confluent BHK-21 cells and incubated at 37° C. for 1 h. After adsorption, cells were washed and overlaid with 1% agarose (SeaPlaque; FMC BioProducts, Rockland, Me.) containing RPMI 1640 with 1% FBS. After incubation for 4 days for JEV and 7 days for DEN-2, cells were fixed with 10% formaldehyde and stained with 0.5% crystal violet. The inhibitors concentrations required to inhibit virus production by 50% ($IC_{50}$) and 90% ($IC_{90}$) were determined.

Indirect immunofluorescence assay (IFA). Cells were fixed in an acetone-methanol (1:1) solution for 3 min and then reacted with a monoclonal antibody (MAb) against JEV NS3 [47] or DEN-2 NS3 [46]. After a wash with phosphate-buffered saline (PBS), cells were further stained with a goat anti-mouse fluorescein isothiocyanate (FITC)-conjugated secondary antibody (Jackson ImmunoResearch, Pennsylvania), and the resulting cells were examined under a Leica fluorescent microscope. The viral protein expressions by IFA were read by Fluorescence Microplate Reader (Molecular Device) with excitation wavelength of 355 nm and the emission wavelength of 488 nm. Data are showed as the percentage versus the infected BHK-21 cells without inhibitor treatment (none, 100%). Cell nuclei were visualized by 4',6'-diamidino-2-phenylindole (DAPI) staining in 0.9% sodium chloride at room temperature for 5 min.

XTT assay. To determine cell viability, a calorimetric XTT-based assay was performed (Cell Proliferation Kit II; Roche). BHK-21 cells in a 96-well plate were incubated with various concentrations of inhibitors for 2 days before the XTT labeling reagent was added to the culture medium. Cells were incubated at 37° C. for about 30 min and then read by an enzyme-linked immunosorbent assay (ELISA) reader at 450 nm (Molecular Devices).

Primary screening for anti-SARS-CoV activity. Vero E6 cells ($2 \times 10^4$ per well) were cultured in a 96-well plate with DMEM supplemented with 10% FBS. The culture medium was removed after 1-day incubation when the cells reached 80%-90% confluence. A solution of 100 μL of DMEM, with 2% FBS containing the compound to be tested, was placed in three wells. Cells were incubated in a $CO_2$ incubator at 37° C. for 2 h and inoculated with SARS-CoV (H. K. strain) at a dose of 100 $TCID_{50}$ per well; the cytopathic morphology of the cells was examined by using an inverted microscope 72 h after infection.

Computer modeling. Docking experiments were conducted by using Autodock 3.0.5 with a Lamarckian Genetic Algorithm (LGA).[48] The crystal structure of a human β-hexosaminidase B complex with a transition state analogue inhibitor, 2-acetamido-2-deoxy-D-glucono-1,5-actone (δ-lactone)[44] was downloaded from RCSB Protein Data Bank (PDB coded lo7a). The chain A of the structure was extracted and utilized in docking simulation. The structure models of inhibitors were built in CAChe (Fujitsu, Japan) and refined by performing an optimized geometry calculation in Mechanics using augmented MM3 parameters and stored in PDB format. MGLTOOLS (Molecular Graphics Lab, Scripps Research Institute)[49] was used for protein structure preparation and parameter creation to meet the input requirements of Autodock. Briefly, essential hydrogen atoms were added to the structure model of hexosaminidase followed by assigning Kollman united atom charges and solvation parameters. Compound molecules were assigned Gasteiger-Marsili charges, merge non-polar H atoms, and defined torsions. Autogrid tool in Autodock3.0.5 was applied to produce energy grids (50×50×50 in xyz directions with 0.375 Å spacing) of various types of compound atoms. These grip maps were centered at the active site where the δ-lactone bound. During docking experiments, each compound was kept flexible and the protein was kept rigid. Solis & Wets' local search method with LGA was applied to generate available conformations of compound structures within the active site. The conformational search was conducted utilizing 0.2 Å quaternion and 2° torsion steps. For each compound structure, a maximum number of $5\times10^6$ energy was evaluated and 50 poses were selected from $2.7\times10^5$ generations per run. Plausible docking modes were selected from the most abundant cluster (RMSD=2.0 Å), which has the strongest affinity energy. Pictures of the final simulated complex were generated in MGLTOOLS.

TABLE 1

Inhibition activities of C1 derivatives of compound 3 against α-glucosidase, β-glucosidase and β-hexosaminidase.

| | α-glucosidase[a] | | β-glucosidase[b] | | N-acetyl-β-hexosaminidse[c] | |
|---|---|---|---|---|---|---|
| Compd | Inhibition (%)[d] | $IC_{50}$ ($K_i$) μM | Inhibition (%)[d] | $IC_{50}$ ($K_i$) μM | Inhibition (%)[d] | $IC_{50}$ ($K_i$) μM |
| Core (4) | 23% | 30 | 32% | 27 | 42% | 62 |
| 5 | 12% | 280 | 20% | >500 | 85% | 0.16 (0.022) |
| 6 | 10% | —[e] | 23% | — | 67% | — |
| 7 | 61% | 4.0 | 52% | 4.8 | 20% | 19 |

TABLE 1-continued

Inhibition activities of C1 derivatives of compound 3 against α-glucosidase, β-glucosidase and β-hexosaminidase.

| Compd | α-glucosidase[a] Inhibition (%)[d] | α-glucosidase[a] IC$_{50}$ (K$_i$) μM | β-glucosidase[b] Inhibition (%)[d] | β-glucosidase[b] IC$_{50}$ (K$_i$) μM | N-acetyl-β-hexosaminidse[c] Inhibition (%)[d] | N-acetyl-β-hexosaminidse[c] IC$_{50}$ (K$_i$) μM |
|---|---|---|---|---|---|---|
| 8 | 20% | — | 31% | — | 50% | — |
| 9 | 27% | — | 37% | — | 53% | — |
| 10 | 16% | | 12% | | 13% | |
| 11 | 41% | — | 55% | — | 6% | — |
| 12 | 19% | | 49% | | 8% | |
| 13 | 19% | — | 59% | — | 3% | — |
| 14 | 51% | | 7% | — | 54% | — |
| 15 | 45% | 100 | 28% | 58 (30) | 31% | 44 |
| 16 | 67% | 19 | 44% | 49 | 10% | 15 |
| 17 | 94% | 0.28 (0.077) | 45% | 92 | 45% | — |
| 18 | 36% | 120 | 53% | 10 (6.2) | 23% | 42 |
| 19 | 82% | — | 15% | — | 14% | — |
| 20 | 85% | 1.2 (0.43) | 23% | 130 | 29% | — |
| 21 | 83% | 11 | 20% | 75 | 27% | 3.2 |
| 22 | 42% | 0.81 | 34% | 260 | 16% | 63 |
| 23 | 63% | 17 | 28% | 92 | 14% | 4.7 |
| 24 | 93% | 0.15 (0.053) | 45% | 92 | 9% | 11 |
| 25 | 56% | — | 63% | — | 17% | — |
| 26 | 31% | — | 52% | — | 17% | — |
| 27 | 26% | — | 55% | — | 6% | — |
| 28 | 27% | 250 | 67% | 2.4 (1.2) | 52% | — |
| 29 | 22% | 280 | 55% | 3.2 (1.4) | 17% | 7.02 |

[a]From baker yeast.
[b]From almonds.
[c]From jack bean.
[d]Inhibition percentage (%) = [enzyme activity (blank) − enzyme activity (inhibitor)]/enzyme activity (blank)
*100%.
[e]Not determined.

TABLE 2

Antiviral activities of different iminocyclitols 36-38.

| | JEV M.O.I. = 0.1 | | DEN M.O.I. = 0.1 | |
|---|---|---|---|---|
| Compd | IC$_{50}$(μM) | IC$_{90}$(μM) | IC$_{50}$(μM) | IC$_{90}$(μM) |
| 36 | 11.3 ± 1.9 | 17.5 ± 0.8 | 11.8 ± 0.2 | 18.0 ± 0.2 |
| 37 | 9.6 ± 0.8 | 18.0 ± 0.2 | 4.7 ± 1.5 | 9.2 ± 0.6 |
| 38 | 7.6 ± 0.1 | 9.7 ± 0.1 | 6.0 ± 0.5 | 9.1 ± 0.3 |

REFERENCES

[1] L. Ellgaard, A. Helenius, *Nature Rev. Mol. Cell Biol.* 2003, 4, 181-191.
[2] N. Asano, *Glycobiology* 2003, 13, 93R-140R.
[3] R. A. Dwek, T. D. Butters, F. M. Platt, N. Zitzmann, N. *Nat. Rev. Drug Discov.* 2002, 1, 65-75.
[4] G. S. Jacob, *Curr. Opin. Struct. Biol.* 1995, 5, 605-611.
[5] W. Lew, X. Chen, C. U. Kim, *Curr. Med. Chem.* 2000, 7, 663-672.
[6] A. Mitrakou, A. E. Tountas, R. J. Raptis, H. Bauer, S. A. Schulz, *Raptis. Diabet. Med.* 1998, 15, 657-660.
[7] L. J. Scott, C. M. Spencer, *Drugs* 2000, 59, 521-549.
[8] P. E. Goss, J. Baptiste, B. Fernandes, M. Baker, J. W. Dennis, J. W. *Cancer Res.* 1994, 54, 1450-1457.
[9] R. A. Gruters, J. J. Neefjes, M. Tersmette, R. E. de Goede, A. Tulp, H. G. Huisman, F. Miedema, H. L. Ploegh, *Nature* 1987, 330, 74-77.
[10] B. D. Walker, M. Kowalski, W. C. Goh, K. Kozarsky, M. Krieger, C. Rosen, L. Rohrschneider, W. A. Haseltine, J. Sodroski, *Proc. Natl. Acad. Sci. U.S.A.* 1987, 84, 8120-8124.
[11] T. M. Block, X. Lu, F. M. Platt, G. R. Foster, W. H. Gerlich, B. S. Blumberg, R. A. Dwek, *Proc. Natl. Acad. Sci. U.S.A.* 1994, 91, 2235-2239.
[12] A. Mehta, S. Carrouee, B. Conyers, R. Jordan, T. Butters, R. A. Dwek, T. M. Block, *Hepatology* 2001, 33, 1488-1495.
[13] D. Durantel, N. Branza-Nichita, S. Carrouee-Durantel, T. D. Butters, R. A. Dwek, N. Zitzmann, *J. Virol.* 2001, 75, 8987-8998.
[14] D. Durantel, S. Carrouee-Durantel, N. Branza-Nichita, R. A. Dwek, N. Zitzmann, *Antimicrob. Agents Chemother.* 2004, 48, 497-504.
[15] M. P. Courageot, M. P. Frenkiel, C. D. Dos Santos, V. Deubel, P. Despres, *J. Virol.* 2000, 74, 564-572.
[16] S.-F. Wu, C.-J. Lee, C.-L. Liao, R. A. Dwek, N. Zitzmann, Y.-L. Lin, *J. Viol.* 2002, 76, 3596-3604.
[17] T. D. Butters, R. A. Dwek, F. M. Platt, *Chem. Rev.* 2000 100, 4683-4696.
[18] J. Q. Fan, *Trends Pharmacol. Sci.* 2003 24, 355-360.
[19] A. E. Stütz, *Iminosugars as Glycosidase Inhibitors-Norjirimycin and Beyond*, Weinheim, Germany: Wiley-VCH, 1999.
[20] A. Welter, G. Dardene, M. Marlier, J. Casimir, *Phytochemistry* 1976, 2, 747-749.
[21] P. J. Card, W. D. Hitz, *J. Org. Chem.* 1985, 50, 891-893.
[22] S. M. Andersen, M. Ebner, C. W. Ekhart, G. Gradnig, G. Legler, I. Lundt, A. E. Stütz, S. G. Withers, T. Wrodnigg, *Carbohydr. Res.* 1997, 301, 155-166.
[23] G. C. Look, C. H. Fotsch, C.-H. Wong, *Acc. Chem. Res.* 1993, 26, 182-190.
[24] C. Saotome, C.-H. Wong, O. Kanie, *Chem. Biol.* 2001, 8, 1061-1070.
[25] M. Takebayashi, S. Iranuma, Y. Kanie, T. Kajimoto, O. Kanie, C.-H. Wong, *J. Org. Chem.* 1999, 64, 5280-5291.

[26] T. M. Wrodigg, F. Diness, C. Gruber, H. Häusler, I. Lundt, K. Rupitz, A. J. Steiner, A. E. Stütz, C. A. Tarling, S. G. Withers, H. Wölfler, *Bioorg. Med. Chem.* 2004, 12, 3458-3495.

[27] C.-F. Chang, C.-W. Ho, C.-Y. Wu, T.-A. Chao, C.-H. Wong, C.-H. Lin, *Chem. Biol.* 2004, 11, 1301-1306.

[28] A. Brik, Y. C. Lin, J. Elder, C.-H. Wong, *Chem. Biol.* 2002, 9, 891-896.

[29] A. R. Shikhman, D. C. Brinson, M. Lotz, *Arthritis Rheum.* 2000, 43, 1307-1314.

[30] J. Liu, A. R. Shikhman, M. K. Lotz, C.-H. Wong, *Chem. Biol.* 2001, 8, 701-711.

[31] V. Perez-Alvarez, R. A. Bobadilla, P. Muriel, *J. Appl. Toxicol.* 2001, 21, 527-531.

[32] J. Wiesner, A. Mitsch, P. Wißner, H. Jomaa, M. Schlitzer, *Bioorg. Med. Chem. Lett.* 2001, 11, 423-424.

[33] F. Natella, M. Nardini, M. Di Felice, C. Scaccini, *J. Agric. Food Chem.* 1999, 47, 1453-1459.

[34] A. Tan, L. van den Broek, S. van Boeckel, H. Ploegh, J. Bolscher, *J. Biol. Chem.* 1991, 266, 14504-15410.

[35] C. L. Jacobs, K. Y. Yarema, L. K. Mahal, D. A. Nauman, N. W. Charters, C. R. Bertozzi, *Meth. Enzymol.* 2000, 327, 260-275.

[36] H. R. Mellor, F. M. Platt, R. A. Dwek, T. D. Butters, *Biochem. J.* 2003, 374, 307-14.

[37] A. Mehta, S. Ouzounov, R. Jordan, E. Simsek, X. Lu, R. M. Moriarty, G. Jacob, R. A. Dwek, T. M. Block, *Antiviral Chem. Chemother.* 2002, 13, 299-304.

[38] T. M. Block, X. Lu, A. Mehta, B. Blumberg, B. Tennant, M. Ebling, B. Korba, D. M. Lansky, G. S. Jacob, R. A. Dwek, *Nature Med.* 1998, 4, 610-614.

[39] C. McGuigan, C. J. Yarnold, G. Jones, S. Velazquez, H. Barucki, A. Brancale, G. Andrei, R. Snoeck, E. De Clercq, J. Balzarini, *J. Med. Chem.* 1999, 42, 4479-4484.

[40] N. Zitzmann, A. S. Mehta, S. Carrouee, T. D. Butters, F. M. Platt, J. McCauley, B. S. Blumberg, R. A. Dwek, T. M. Block, *Proc. Natl. Acad. Sci. U.S.A.* 1999, 96, 11878-11882.

[41] C.-Y. Wu, J.-T. Jan, S.-H. Ma, C.-J. Kuo, H.-F. Juan, Y.-S. E. Cheng, H.-H. Hsu, H.-C. Huang, D. Wu, A. Brik, F.-S. Liang, R.-S. Liu, J.-M. Fang, S.-T. Chen, P.-H. Liang, C.-H. Wong, *Proc. Natl. Acad. Sci. U.S.A.* 2004, 101, 10012-10017.

[42] J. Liu, M. M. D. Numa, H. Liu, S.-J. Huang, P. Sears, A. R. Shikhman, C.-H. Wong, *J. Org. Chem.* 2004, 69, 6273-6283.

[43] T. Maier, N. Strater, C. G. Schuette, R. Klingenstein, K. Sandhoff, W. Saenger, *J. Mol. Biol.* 2003, 328, 669-681

[44] A. Bulow, I. W. Plesner, M. Bols, *J. Am. Chem. Soc.* 2000, 122, 8567-8568.

[45] L. K. Chen, Y. L. Lin, C. L. Liao, C. G. Lin, Y. L. Huang, C. T. Yeh, S. C. Lai, J. T. Jan, C. Chin. *Virology* 1996, 223, 79-88.

[46] Y. L. Lin, C. L. Liao, L. K. Chen, C. T. Yeh, C. I. Liu, S. H. Ma, Y. Y. Huang, Y. L. Huang, C. L. Kao, C. C. King. *J. Virol.* 1998, 72, 9729-9737.

[47] L. K. Chen, C. L. Liao, C. G. Lin, S. C. Lai, C. I. Liu, S. H. Ma, Y. Y. Huang, Y. L. Lin, *Virology* 1996, 217, 220-229.

[48] G. M. Morris, D. S. Goodsell, R. S. Halliday, R. Huey, W. E. Hart, R. K. Belew, A. J. Olson, *J. Comput. Chem.* 1998, 19, 1639-1662.

[49] MGLTOOLS: http://www.scripps.edu/~sanner/python. Molecular Graphics Lab (MGL) of the Scripps Research Institute.

What is claimed is:

1. An inhibitor of hexoaminidase or glucosidase represented by the following structure:

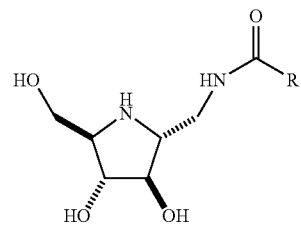

wherein R is

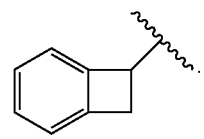

2. An inhibitor of hexoaminidase or glucosidase represented by the following structure:

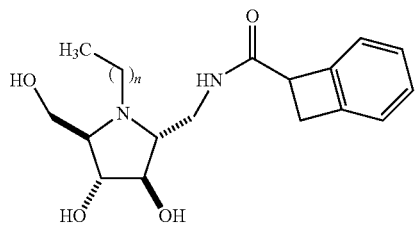

wherein n is an integer ranging from 3-11.

3. A method of treating infection of Japanese encephalitis virus or dengue virus serotype 2 comprising administering to a patient in need thereof an effective amount of compound selected from claim 2.

4. A method of treating arthritis comprising the step of administering an inhibitor as in claim 2 to said subject of sufficient quantity for inhibiting hexoaminidase or glucosidase activity within said subject.

5. A method of treating arthritis comprising the step of administering an inhibitor as in claim 4 to said subject of sufficient quantity for inhibiting hexoaminidase or glucosidase activity within said subject.

* * * * *